(12) United States Patent
Yang

(10) Patent No.: US 12,332,391 B2
(45) Date of Patent: Jun. 17, 2025

(54) DETECTOR SYSTEMS AND IMAGING DEVICES

(71) Applicant: SHANGHAI UNITED IMAGING HEALTHCARE CO., LTD., Shanghai (CN)

(72) Inventor: Sihang Yang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 311 days.

(21) Appl. No.: 18/172,262

(22) Filed: Feb. 21, 2023

(65) Prior Publication Data

US 2023/0266487 A1    Aug. 24, 2023

(30) Foreign Application Priority Data

Feb. 21, 2022   (CN) .......................... 202210158821.2

(51) Int. Cl.
| | |
|---|---|
| *A61B 6/03* | (2006.01) |
| *G01T 1/20* | (2006.01) |
| *G01T 1/29* | (2006.01) |
| *G01T 1/202* | (2006.01) |

(52) U.S. Cl.
CPC .......... *G01T 1/20184* (2020.05); *A61B 6/037* (2013.01); *G01T 1/20187* (2020.05); *G01T 1/2985* (2013.01); *G01T 1/202* (2013.01)

(58) Field of Classification Search
CPC ...................................................... A61B 6/037
See application file for complete search history.

(56) References Cited

U.S. PATENT DOCUMENTS

| | | |
|---|---|---|
| 7,378,659 B2 | 5/2008 | Burr et al. |
| 8,880,144 B2 | 11/2014 | Kang et al. |
| 2013/0153774 A1 | 6/2013 | Hughes et al. |
| 2019/0064369 A1* | 2/2019 | Chen .................. G01N 21/6408 |

\* cited by examiner

*Primary Examiner* — David P Porta
*Assistant Examiner* — Shun Lee
(74) *Attorney, Agent, or Firm* — METIS IP LLC

(57) ABSTRACT

The embodiments of the present disclosure provide detector systems and imaging devices. The system may include a first photosensor array, a second photosensor array and a readout module. A position of the first photosensor array may be opposite to a position of the second photosensor array. Configurations of the first photosensor array and the second photosensor array may be the same. The first photosensor array and the second photosensor array may be configured to output electrical signals related to radiated photons, respectively. The readout module may include a first readout unit and a second readout unit. Configurations of the first readout unit and the second readout unit may be the same. The first readout unit and the second readout unit may be configured to process the electrical signals.

20 Claims, 13 Drawing Sheets

| | | | | | | | | | | | | | | | |
|---|---|---|---|---|---|---|---|---|---|---|---|---|---|---|---|
| P3 | O3 | N3 | M3 | L3 | K3 | J3 | I3 | H3 | G3 | F3 | E3 | D3 | C3 | B3 | A3 |
| P4 | O4 | N4 | M4 | L4 | K4 | J4 | I4 | H4 | G4 | F4 | E4 | D4 | C4 | B4 | A4 |
| P5 | O5 | N5 | M5 | L5 | K5 | J5 | I5 | H5 | G5 | F5 | E5 | D5 | C5 | B5 | A5 |
| P6 | O6 | N6 | M6 | L6 | K6 | J6 | I6 | H6 | G6 | F6 | E6 | D6 | C6 | B6 | A6 |
| P7 | O7 | N7 | M7 | L7 | K7 | J7 | I7 | H7 | G7 | F7 | E7 | D7 | C7 | B7 | A7 |
| P8 | O8 | N8 | M8 | L8 | K8 | J8 | I8 | H8 | G8 | F8 | E8 | D8 | C8 | B8 | A8 |
| P9 | O9 | N9 | M9 | L9 | K9 | J9 | I9 | H9 | G9 | F9 | E9 | D9 | C9 | B9 | A9 |
| P10 | O10 | N10 | M10 | L10 | K10 | J10 | I10 | H10 | G10 | F10 | E10 | D10 | C10 | B10 | A10 |
| P11 | O11 | N11 | M11 | L11 | K11 | J11 | I11 | H11 | G11 | F11 | E11 | D11 | C11 | B11 | A11 |
| P12 | O12 | N12 | M12 | L12 | K12 | J12 | I12 | H12 | G12 | F12 | E12 | D12 | C12 | B12 | A12 |
| P13 | O13 | N13 | M13 | L13 | K13 | J13 | I13 | H13 | G13 | F13 | E13 | D13 | C13 | B13 | A13 |
| P14 | O14 | N14 | M14 | L14 | K14 | J14 | I14 | H14 | G14 | F14 | E14 | D14 | C14 | B14 | A14 |
| P15 | O15 | N15 | M15 | L15 | K15 | J15 | I15 | H15 | G15 | F15 | E15 | D15 | C15 | B15 | A15 |
| P16 | O16 | N16 | M16 | L16 | K16 | J16 | I16 | H16 | G16 | F16 | E16 | D16 | C16 | B16 | A16 |

FIG. 8

| P3 | O3 | N3 | M3 | L3 | K3 | J3 | I3 | H3 | G3 | F3 | E3 | D3 | C3 | B3 | A3 |
|----|----|----|----|----|----|----|----|----|----|----|----|----|----|----|----|
| P4 | O4 | N4 | M4 | L4 | K4 | J4 | I4 | H4 | G4 | F4 | E4 | D4 | C4 | B4 | A4 |
| P5 | O5 | N5 | M5 | L5 | K5 | J5 | I5 | H5 | G5 | F5 | E5 | D5 | C5 | B5 | A5 |
| P6 | O6 | N6 | M6 | L6 | K6 | J6 | I6 | H6 | G6 | F6 | E6 | D6 | C6 | B6 | A6 |
| P7 | O7 | N7 | M7 | L7 | K7 | J7 | I7 | H7 | G7 | F7 | E7 | D7 | C7 | B7 | A7 |
| P8 | O8 | N8 | M8 | L8 | K8 | J8 | I8 | H8 | G8 | F8 | E8 | D8 | C8 | B8 | A8 |
| P9 | O9 | N9 | M9 | L9 | K9 | J9 | I9 | H9 | G9 | F9 | E9 | D9 | C9 | B9 | A9 |
| P10 | O10 | N10 | M10 | L10 | K10 | J10 | I10 | H10 | G10 | F10 | E10 | D10 | C10 | B10 | A10 |
| P11 | O11 | N11 | M11 | L11 | K11 | J11 | I11 | H11 | G11 | F11 | E11 | D11 | C11 | B11 | A11 |
| P12 | O12 | N12 | M12 | L12 | K12 | J12 | I12 | H12 | G12 | F12 | E12 | D12 | C12 | B12 | A12 |
| P13 | O13 | N13 | M13 | L13 | K13 | J13 | I13 | H13 | G13 | F13 | E13 | D13 | C13 | B13 | A13 |
| P14 | O14 | N14 | M14 | L14 | K14 | J14 | I14 | H14 | G14 | F14 | E14 | D14 | C14 | B14 | A14 |
| P15 | O15 | N15 | M15 | L15 | K15 | J15 | I15 | H15 | G15 | F15 | E15 | D15 | C15 | B15 | A15 |
| P16 | O16 | N16 | M16 | L16 | K16 | J16 | I16 | H16 | G16 | F16 | E16 | D16 | C16 | B16 | A16 |
| P17 | O17 | N17 | M17 | L17 | K17 | J17 | I17 | H17 | G17 | F17 | E17 | D17 | C17 | B17 | A17 |
| P18 | O18 | N18 | M18 | L18 | K18 | J18 | I18 | H18 | G18 | F18 | E18 | D18 | C18 | B18 | A18 |

FIG. 9

| P3 | O3 | N3 | M3 | L3 | K3 | J3 | I3 | H3 | G3 | F3 | E3 | D3 | C3 | B3 | A3 |
|----|----|----|----|----|----|----|----|----|----|----|----|----|----|----|----|
| P4 | O4 | N4 | M4 | L4 | K4 | J4 | I4 | H4 | G4 | F4 | E4 | D4 | C4 | B4 | A4 |
| P5 | O5 | N5 | M5 | L5 | K5 | J5 | I5 | H5 | G5 | F5 | E5 | D5 | C5 | B5 | A5 |
| P6 | O6 | N6 | M6 | L6 | K6 | J6 | I6 | H6 | G6 | F6 | E6 | D6 | C6 | B6 | A6 |
| P7 | O7 | N7 | M7 | L7 | K7 | J7 | I7 | H7 | G7 | F7 | E7 | D7 | C7 | B7 | A7 |
| P8 | O8 | N8 | M8 | L8 | K8 | J8 | I8 | H8 | G8 | F8 | E8 | D8 | C8 | B8 | A8 |
| P9 | O9 | N9 | M9 | L9 | K9 | J9 | I9 | H9 | G9 | F9 | E9 | D9 | C9 | B9 | A9 |
| P10 | O10 | N10 | M10 | L10 | K10 | J10 | I10 | H10 | G10 | F10 | E10 | D10 | C10 | B10 | A10 |
| P11 | O11 | N11 | M11 | L11 | K11 | J11 | I11 | H11 | G11 | F11 | E11 | D11 | C11 | B11 | A11 |
| P12 | O12 | N12 | M12 | L12 | K12 | J12 | I12 | H12 | G12 | F12 | E12 | D12 | C12 | B12 | A12 |
| P13 | O13 | N13 | M13 | L13 | K13 | J13 | I13 | H13 | G13 | F13 | E13 | D13 | C13 | B13 | A13 |
| P14 | O14 | N14 | M14 | L14 | K14 | J14 | I14 | H14 | G14 | F14 | E14 | D14 | C14 | B14 | A14 |
| P15 | O15 | N15 | M15 | L15 | K15 | J15 | I15 | H15 | G15 | F15 | E15 | D15 | C15 | B15 | A15 |
| P16 | O16 | N16 | M16 | L16 | K16 | J16 | I16 | H16 | G16 | F16 | E16 | D16 | C16 | B16 | A16 |
| P17 | O17 | N17 | M17 | L17 | K17 | J17 | I17 | H17 | G17 | F17 | E17 | D17 | C17 | B17 | A17 |
| P18 | O18 | N18 | M18 | L18 | K18 | J18 | I18 | H18 | G18 | F18 | E18 | D18 | C18 | B18 | A18 |

FIG. 10

| | 1110-1 | | | | 1120-3 | | | | | | | | 1120-1 | |
|---|---|---|---|---|---|---|---|---|---|---|---|---|---|---|
| P3 | O3 | N3 | M3 | L3 | K3 | J3 | I3 | H3 | G3 | F3 | E3 | D3 | C3 | B3 | A3 |
| P4 | O4 | N4 | M4 | L4 | K4 | J4 | I4 | H4 | G4 | F4 | E4 | D4 | C4 | B4 | A4 |
| P5 | O5 | N5 | M5 | L5 | K5 | J5 | I5 | H5 | G5 | F5 | E5 | D5 | C5 | B5 | A5 |
| P6 | O6 | N6 | M6 | L6 | K6 | J6 | I6 | H6 | G6 | F6 | E6 | D6 | C6 | B6 | A6 |
| P7 | O7 | N7 | M7 | L7 | K7 | J7 | I7 | H7 | G7 | F7 | E7 | D7 | C7 | B7 | A7 |
| P8 | O8 | N8 | M8 | L8 | K8 | J8 | I8 | H8 | G8 | F8 | E8 | D8 | C8 | B8 | A8 |
| P9 | O9 | N9 | M9 | L9 | K9 | J9 | I9 | H9 | G9 | F9 | E9 | D9 | C9 | B9 | A9 |
| P10 | O10 | N10 | M10 | L10 | K10 | J10 | I10 | H10 | G10 | F10 | E10 | D10 | C10 | B10 | A10 |
| P11 | O11 | N11 | M11 | L11 | K11 | J11 | I11 | H11 | G11 | F11 | E11 | D11 | C11 | B11 | A11 |
| P12 | O12 | N12 | M12 | L12 | K12 | J12 | I12 | H12 | G12 | F12 | E12 | D12 | C12 | B12 | A12 |
| P13 | O13 | N13 | M13 | L13 | K13 | J13 | I13 | H13 | G13 | F13 | E13 | D13 | C13 | B13 | A13 |
| P14 | O14 | N14 | M14 | L14 | K14 | J14 | I14 | H14 | G14 | F14 | E14 | D14 | C14 | B14 | A14 |
| P15 | O15 | N15 | M15 | L15 | K15 | J15 | I15 | H15 | G15 | F15 | E15 | D15 | C15 | B15 | A15 |
| P16 | O16 | N16 | M16 | L16 | K16 | J16 | I16 | H16 | G16 | F16 | E16 | D16 | C16 | B16 | A16 |
| P17 | O17 | N17 | M17 | L17 | K17 | J17 | I17 | H17 | G17 | F17 | E17 | D17 | C17 | B17 | A17 |
| P18 | O18 | N18 | M18 | L18 | K18 | J18 | I18 | H18 | G18 | F18 | E18 | D18 | C18 | B18 | A18 |

| P3 | O3 | N3 | M3 | L3 | K3 | J3 | I3 | H3 | G3 | F3 | E3 | D3 | C3 | B3 | A3 |
|---|---|---|---|---|---|---|---|---|---|---|---|---|---|---|---|
| P4 | O4 | N4 | M4 | L4 | K4 | J4 | I4 | H4 | G4 | F4 | E4 | D4 | C4 | B4 | A4 |
| P5 | O5 | N5 | M5 | L5 | K5 | J5 | I5 | H5 | G5 | F5 | E5 | D5 | C5 | B5 | A5 |
| P6 | O6 | N6 | M6 | L6 | K6 | J6 | I6 | H6 | G6 | F6 | E6 | D6 | C6 | B6 | A6 |
| P7 | O7 | N7 | M7 | L7 | K7 | J7 | I7 | H7 | G7 | F7 | E7 | D7 | C7 | B7 | A7 |
| P8 | O8 | N8 | M8 | L8 | K8 | J8 | I8 | H8 | G8 | F8 | E8 | D8 | C8 | B8 | A8 |
| P9 | O9 | N9 | M9 | L9 | K9 | J9 | I9 | H9 | G9 | F9 | E9 | D9 | C9 | B9 | A9 |
| P10 | O10 | N10 | M10 | L10 | K10 | J10 | I10 | H10 | G10 | F10 | E10 | D10 | C10 | B10 | A10 |
| P11 | O11 | N11 | M11 | L11 | K11 | J11 | I11 | H11 | G11 | F11 | E11 | D11 | C11 | B11 | A11 |
| P12 | O12 | N12 | M12 | L12 | K12 | J12 | I12 | H12 | G12 | F12 | E12 | D12 | C12 | B12 | A12 |
| P13 | O13 | N13 | M13 | L13 | K13 | J13 | I13 | H13 | G13 | F13 | E13 | D13 | C13 | B13 | A13 |
| P14 | O14 | N14 | M14 | L14 | K14 | J14 | I14 | H14 | G14 | F14 | E14 | D14 | C14 | B14 | A14 |
| P15 | O15 | N15 | M15 | L15 | K15 | J15 | I15 | H15 | G15 | F15 | E15 | D15 | C15 | B15 | A15 |
| P16 | O16 | N16 | M16 | L16 | K16 | J16 | I16 | H16 | G16 | F16 | E16 | D16 | C16 | B16 | A16 |
| P17 | O17 | N17 | M17 | L17 | K17 | J17 | I17 | H17 | G17 | F17 | E17 | D17 | C17 | B17 | A17 |
| P18 | O18 | N18 | M18 | L18 | K18 | J18 | I18 | H18 | G18 | F18 | E18 | D18 | C18 | B18 | A18 |

DETECTOR SYSTEMS AND IMAGING DEVICES

CROSS-REFERENCE TO RELATED DISCLOSURES

This application claims priority of Chinese Patent Application No. 202210158821.2, entitled "DETECTOR SYSTEMS AND IMAGING DEVICES", filed on Feb. 21, 2022, the contents of which are incorporated herein by reference.

TECHNICAL FIELD

The present disclosure generally relates to the field of medical devices, in particular to detector systems and imaging devices.

BACKGROUND

Emission Computed Tomography (ECT) detector is a detection device configured to measure or detect radiation photon energy, which is widely used in the field of nuclear medicine. For example, positron emission tomography (PET) and single-photon emission computed tomography (SPECT) both use ECT detectors. The double-ended readout detector may read outputs of the photosensor array located at the top and the bottom of the detector crystal, and locate the depth where the radiation photon occurs in the detector crystal based on the difference between the readout value of the top and the readout value of the bottom of the detector crystal, thereby eliminating errors to improve the resolution and the sensitivity of the detector. In some double-ended readout detectors, the structure of the double-ended photosensor array plate and the signal readout plate are separately designed, and the way of coding, channel extraction and signal processing of the photosensor array are relatively complicated, having a high cost and poor maintainability.

Therefore, it is desired to provide detector systems and imaging devices to reduce the difficulty of design and maintenance, and reduce costs of maintenance and research and development.

SUMMARY

One of the embodiments of the present disclosure may provide a detector system. The system may include a first photosensor array and a second photosensor array. A position of the first photosensor array may be opposite to a position of the second photosensor array. Configurations of the first photosensor array and the second photosensor array may be the same. The first photosensor array and the second photosensor array may be configured to output electrical signals related to radiated photons, respectively. The system may further include a readout module. The readout module may include a first readout unit and a second readout unit. The first readout unit may be configured to read out signals of detection units of a first part in the first photosensor array and signals of detection units of a third part in the second photosensor array. The second readout unit may be configured to read out signals of detection units of a second part in the first photosensor array and signals of detection units of a fourth part in the second photosensor array.

In some embodiments of the present disclosure, an amount of the detection units of the first part, an amount of the detection units of the second part, an amount of the detection units of the third part, an amount of the detection units of the fourth part may be equal.

In some embodiments of the present disclosure, configurations of the first readout unit and the second readout unit may be the same.

In some embodiments of the present disclosure, shapes of the first part and the second part are symmetrical about a center, and shapes of the third part and the fourth part may be symmetrical about the center.

In some embodiments of the present disclosure, the first photosensor array may be divided into the first part and the second part along a first direction.

In some embodiments of the present disclosure, the second photosensor array may be divided into the third part and the fourth part along the first direction.

In some embodiments of the present disclosure, the detection units of the first part may be encoded in a same way as the detection units of the third part. The detection units of the second part may be encoded in a same way as the detection units of the fourth part.

In some embodiments of the present disclosure, a coding sequence of the detection units of the first part may be symmetrical to a coding sequence of the detection units of the third part with respect to the first direction. A coding sequence of the detection units of the second part may be symmetrical to a coding sequence of the detection units of the fourth part with respect to the first direction.

In some embodiments of the present disclosure, the detection units of the first part may be encoded in a same way as the detection units of the fourth part, and the detection units of the second part may be encoded in a same way as the detection units of the third part.

In some embodiments of the present disclosure, a coding sequence of the detection units of the first part may be symmetrical to a coding sequence of the detection units of the fourth part with respect to a second direction. A coding sequence of the detection units of the second part may be symmetrical to a coding sequence of the detection units of the third part with respect to the second direction.

In some embodiments of the present disclosure, each of the detection units of the first part, the second part, the third part and the fourth part may include at least two discontinuously distributed detection units.

In some embodiments of the present disclosure, shapes of the first part and the second part may be asymmetric and shapes of the third part and the fourth part may be asymmetric.

In some embodiments of the present disclosure, the first photosensor array may be divided into the first part and the second part according to a first preset rule. The first preset rule may include that a boundary between the first part and the second part is discontinuous.

In some embodiments of the present disclosure, the second photosensor array may be divided into the third part and the fourth part according to a second preset rule. The second preset rule may include that a boundary between the third part and the fourth part is discontinuous.

In some embodiments of the present disclosure, an amount of the detection units of the first part may be not equal to an amount of the detection units of the second part. An amount of the detection units of the third part may be not equal to an amount of the detection units of the fourth part. The amount of the detection units of the first part may be equal to the amount of the detection units of the fourth part. The amount of the detection units of the second part may be equal to the amount of the detection units of the third part.

In some embodiments of the present disclosure, the detection units of the first part, the detection units of the third part, the detection units of the second part, and the detection units of the fourth part may be encoded in different ways.

In some embodiments of the present disclosure, configurations of the first readout unit and the second readout unit may be different.

In some embodiments of the present disclosure, the first part may include a first interface. The second part may include a second interface. The third part may include a third interface. The fourth part may include a fourth interface. The readout module may be connected to the first photosensor array and the second photosensor array through the first interface, the second interface, the third interface and the fourth interface.

In some embodiments of the present disclosure, the first photosensor array may include a first surface and a second surface. A position of the first surface may be opposite to a position of the second surface. The second photosensor array may include a third surface and a fourth surface. A position of the third surface may be opposite to a position of the fourth surface. The first interface and the second interface may be arranged on the first surface of the first photosensor array. The third interface and the fourth interface may be arranged on the third surface of the second photosensor array. The position of the second surface of the first photosensor array may be opposite to the position of the fourth surface of the second photosensor array.

One of the embodiments of the present disclosure may provide an imaging device. The imaging device may include a plurality of detector systems arranged around an axis and surrounding a cylindrical scanning area.

In some embodiments of the present disclosure, through the preset way of coding, using the photosensor array plate with the same structure at both ends may realize the double-ended readout, and the uniformity of photosensor array plates of the detector system in the medical imaging device (e.g., PET, SPECT) has been successfully realized. By using the same readout plate at both ends under the preset way of coding, the multiplexing of the readout plate is realized, which reduces the difficulty of design and maintenance of the detector system in medical imaging device, and reduces costs of maintenance and research and development of the medical imaging device, which improves the maintainability of the device and achieves better economic benefits.

BRIEF DESCRIPTION OF THE DRAWINGS

The present disclosure may be further illustrated by way of exemplary embodiments, which may be described in detail with the accompanying drawings. These embodiments are not limiting, and in these embodiments, the same number indicates a similar structure, wherein:

FIG. 8 is a schematic diagram illustrating a photosensor array according to some embodiments of the present disclosure;

FIG. 9 is a schematic diagram illustrating a photosensor array according to some embodiments of the present disclosure;

FIG. 10 is a schematic diagram illustrating a photosensor array according to some embodiments of the present disclosure;

FIG. 11 is a schematic diagram illustrating a photosensor array according to some embodiments of the present disclosure;

FIG. 12 are schematic diagrams illustrating photosensor arrays according to some embodiments of the present disclosure.

DETAILED DESCRIPTION

Figure 1:
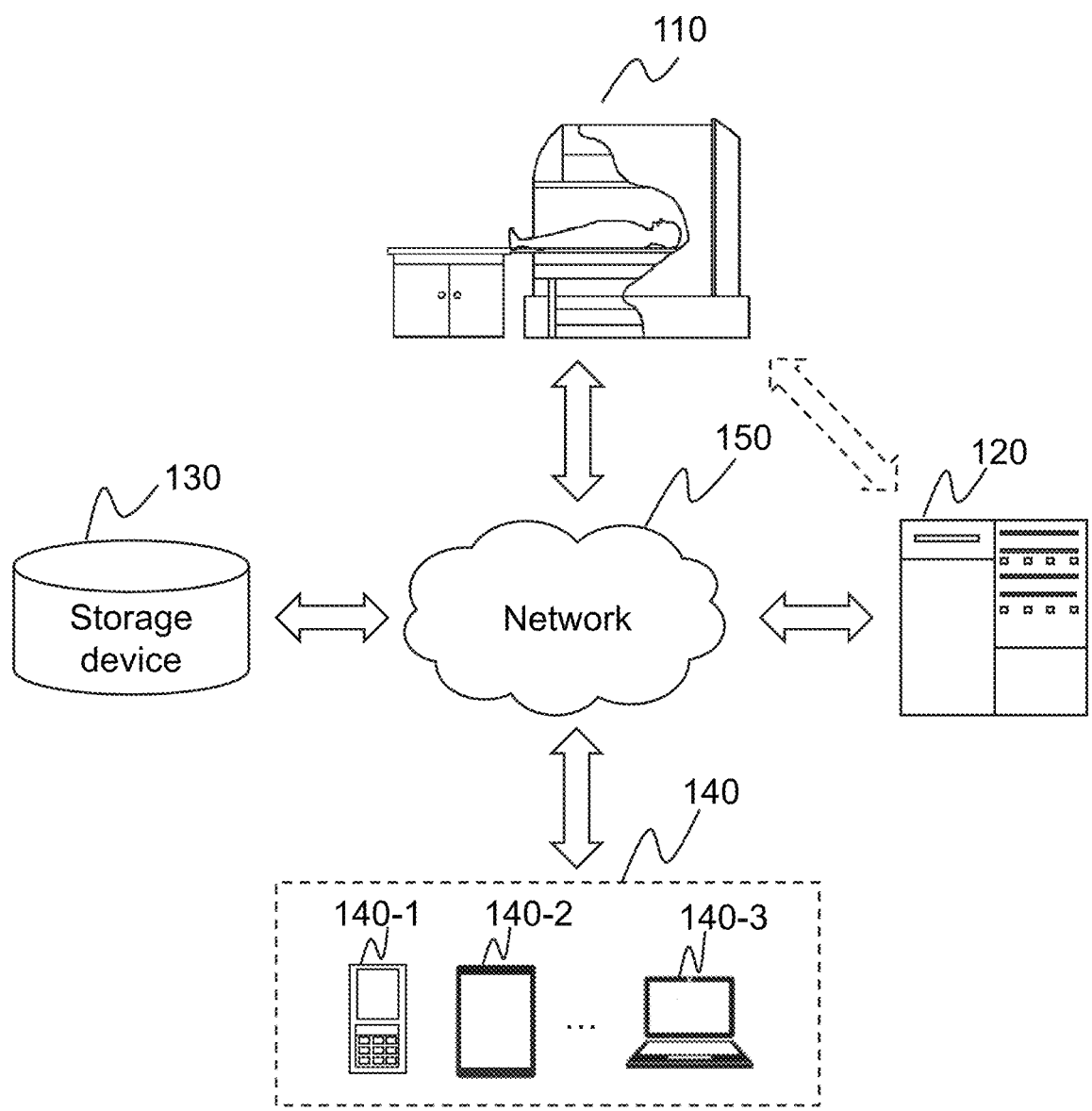
FIG. 1 is a schematic diagram illustrating an application scenario of a detector system according to some embodiments of the present disclosure.

In order to more clearly illustrate the technical solutions of the embodiments of the present disclosure, the following may briefly introduce the drawings that demand to be used in the description of the embodiments. Obviously, the drawings in the following description are only some examples or embodiments of the disclosure. For those of ordinary skill in the art, without creative work, the disclosure may be applied to other similar scenarios according to these drawings. Unless it is obvious from the language environment or otherwise stated, the same reference numbers in the drawings represent the same structure or operation.

It should be understood that the "system", "device", "unit" and/or "module" used herein is a method for distinguishing different assemblies, elements, parts, portions, or assemblies of different levels. However, if other words may achieve the same purpose, the words may be replaced by other expressions.

As shown in the present disclosure and the claims, unless the context clearly suggests exceptional circumstances, the words "a", "an", and/or "the" do not only specifically refer to the singular form, but further include the plural for. Generally speaking, the terms "including," "includes," "include," "comprise," "comprises," and "comprising," only suggest that the operations and/or elements that have been clearly identified are included, but these operations and/or elements do not constitute an exclusive list, and the method, system, or device may further include other operations or elements.

Flowcharts are used in the present disclosure to describe operations performed by a system according to an embodiment of the present disclosure. It should be understood that the preceding or following operations are not necessarily performed in the exact order. Instead, the various operations may be processed in reverse order or simultaneously. Further, other operations may be added to these procedures, or an operation or operations may be removed from these procedures.

In some application scenarios, a medical imaging device may include the detector system disclosed in the present disclosure, thereby realizing the uniformity of the photosensor array plate and the signal readout plate, thereby reducing the difficulty of design and maintenance, reducing costs of maintenance and research, improving maintainability of the device, thus achieving better economic benefits.

FIG. 1 is a schematic diagram illustrating an application scenario of a detector system according to some embodiments of the present disclosure.

As shown in FIG. 1, in some embodiments, the system 100 may include a medical imaging device 110, a processing device 120, a storage device 130, a terminal 140, and a network 150.

The medical imaging device 110 may refer to a device that reproduces internal structures of a target object as an image by using different medias in medicine. In some embodiments, the target object may be a living body, such as a patient, an animal, etc., or an artificial object, such as a phantom. Alternatively, the target object may be a specific part of the patient, such as, an organ and/or a tissue. In some embodiments, the medical imaging device 110 may be any medical device that includes detectors and uses radionuclides to image or treat designated body parts of a patient, such as SPECT, PET, PET-CT, MRI (magnetic resonance imaging)-PET, SPECT-CT, etc. The medical imaging device 110 provided above is for illustration purposes only, and is not intended to limit its scope. The detector in the medical imaging device 110 may receive radiations of radiation sources, and measure the received radiations. In some embodiments, the medical imaging device 110 may include a plurality of detector systems, and the plurality of detector systems may be arranged around an axis and surround a cylindrical scanning area. In some embodiments, the medical imaging device 110 may obtain medical image data through scanning and send the obtained medical image data to the processing device 120. The medical imaging device 110 may receive instructions sent by an operator through the terminal 140, and perform related operations according to the instructions, such as irradiation and imaging. In some embodiments, the medical imaging device 110 may exchange data and/or information with other assemblies in the system 100 (e.g., the processing device 120, the storage device 130, and the terminal 140) through the network 150. In some embodiments, the medical imaging device 110 may be directly connected with other assemblies in the system 100.

The processing device 120 may process data and/or information obtained from other devices or system assemblies. In some embodiments, the processing device 120 may process medical imaging data obtained from the medical imaging device 110. In some embodiments, the processing device 120 may retrieve stored data and/or information from the storage device 130. In some embodiments, the processing device 120 may include one or more sub-processing devices (e.g., a single-core processing device or a multi-core processing device).

The storage device 130 may store data or information generated by other devices. In some embodiments, the storage device 130 may store data and/or information generated by other assemblies in the system 100 (e.g., the medical imaging device 110, the processing device 120). The storage device 130 may include one or more storage assemblies, and each storage assembly may be an independent device or a part of other devices. The storage device may be a local device with respect to other system assemblies, or communicate with other system assemblies through the cloud.

The terminal 140 may control operations of the medical imaging device 110. The operator may issue operation instructions to the medical imaging device 110 through the terminal 140, so that the medical imaging device 110 performs specified operations. For example, a specified body part of a patient may be irradiated and imaged. In some embodiments, the terminal 140 may be one of a mobile device 140-1, a tablet computer 140-2, a laptop computer 140-3, a desktop computer and other devices with input and/or output functions, or any combination thereof.

The network 150 may connect various assemblies of the system and/or connect assemblies of the system with external resources. The network 150 may enable communication between the various assemblies and with other assemblies outside the system to facilitate the exchange of data and/or information. In some embodiments, one or more assemblies in the system 100 (e.g., the medical imaging device 110, the processing device 120, the storage device 130, and the terminal 140) may send data and/or information to other assemblies through the network 150. In some embodiments, the network 150 may be a wired network or a wireless network.

It should be noted that the above descriptions are provided for illustrative purposes only and are not intended to limit the scope of the present disclosure. Those skilled in the art may make various changes and modifications under the guidance of contents of the present disclosure. The features, structures, methods, and other features of the exemplary embodiments described in the present disclosure may be combined in various ways to obtain additional and/or alternative exemplary embodiments. For example, the processing device 120 may be based on a cloud computing platform, such as a public cloud, a private cloud, a community and a hybrid cloud, or the like. However, these changes and modifications do not depart from the scope of the present disclosure.

Figure 2:
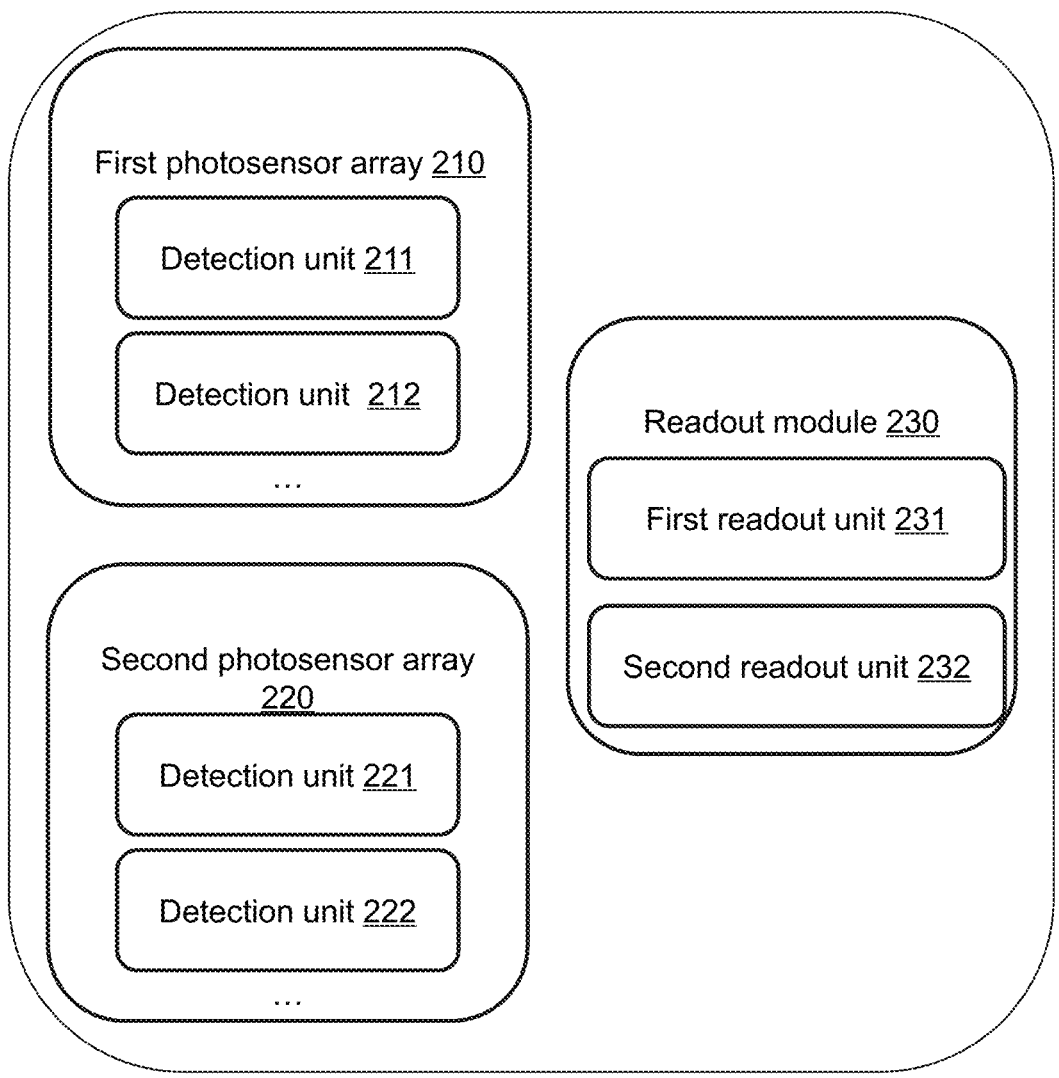
FIG. 2 is a schematic diagram illustrating a detector system according to some embodiments of the present disclosure.

FIG. 2 is a schematic diagram illustrating a detector system according to some embodiments of the present disclosure.

As shown in FIG. 2, in some embodiments, a detector system 200 may include a double-ended readout detector. The double-ended readout detector may include a first photosensor array 210, a second photosensor array 220 and a readout module 230.

In some embodiments, the detector system 200 may include one or more photosensor arrays each of which includes a plurality of sensors, such as the first photosensor array 210 and the second photosensor array 220. A photosensor array may include a plurality of detection units (also referred to as sensors or sensor units), and each detection unit may be an independent sensor (photoelectric conversion element), such as a photomultiplier tube, an avalanche photodiode, and a silicon photomultiplier (SiPM).

In some embodiments, a plurality of detection units adjacent to each other may form one detector unit (a combination of detection units), and the detector unit may be the smallest functional unit to detect the depth of the radiation photon occurs in the detector crystal. For example, as shown in FIG. 8, 2*2 detection units $$\begin{bmatrix} P3 & O3 \\ P4 & O4 \end{bmatrix}$$

may form one detector unit. In some embodiments, the photosensor array may be formed by detector units in fixed size. For example, the photosensor array shown in FIG. 8 may include 14*16 detection units in all, which are grouped into 7*8 detector units in the size of 2*2. For another example, the photosensor array shown in FIG. 9 may include 16*16 detection units in all, which are grouped into 8*8 detector units in the size of 2*2. In some embodiments, a detector unit may be of another size, such as, 2*3, 3*3. The present disclosure may take the detector units with a size of 2*2 as an example for illustration, which is for illustration purposes only, not as a limitation on the detector unit.

In some embodiments, a position of the first photosensor array 210 may be opposite to a position of the second photosensor array 220, and configurations of the first photosensor array 210 and the second photosensor array 230 may be the same. That the position of the first photosensor array 210 is opposite to the position of the second photosensor array 220 may indicate that one surface of the first photosensor array 210 is placed opposite to one surface of the second photosensor array 220. The same configuration may mean that structures and the ways of coding of the first photosensor array 210 and the second photosensor array 220 are the same. For example, the first photosensor array 210 and the second photosensor array 220 may be physically identical. The first photosensor array 210 may be flipped by 180 degrees around a certain axis, and the structure and the way of coding of the flipped first photosensor array 210 may be exactly the same as the structure and the way of coding of the second photosensor array 220. For another example, when preparing the second photosensor array 220, the second photosensor array 220 photosensor array may be obtained by duplicating the first photosensor array 210, resulting in being identical to the first photosensor array 210. In some embodiments, the same way of coding may refer to the same coding sequence. For example, the first photosensor array 210 and the second photosensor array 220 may both include 1416 detection units as shown in FIG. 8, and the way of coding may both be $$\begin{bmatrix} P3 & \ldots & A3 \\ \ldots & \ldots & \ldots \\ P16 & \ldots & A16 \end{bmatrix}.$$

For another example, the first photosensor array 210 and the second photosensor array 220 may both include 16*16 detection units as shown in FIG. 9, and the way of coding may both be $$\begin{bmatrix} P3 & \ldots & A3 \\ \ldots & \ldots & \ldots \\ P18 & \ldots & A18 \end{bmatrix}.$$

In some embodiments of the present disclosure, by using the same photosensor array plate, the uniformity of the photosensor arrays is realized, which reduces the complexity of design and maintenance of the detector system in the medical imaging device (e.g., PET, SPECT), and effectively reduces costs of design and maintenance.

In some embodiments, the first photosensor array 210 and the second photosensor array 220 may be configured to output electrical signals related to radiation photons (e.g., γ photons). In some embodiments, the sensors in the first photosensor array 210 and the second photosensor array 220 may be any sensors capable of receiving scintillation lights and converting the scintillation lights into electrical signals, such as photomultiplier tubes, avalanche photodiodes, silicon photomultipliers (SiPM), etc., and any combination thereof.

In some embodiments, the detector system 200 may further include scintillation crystal arrays (not shown in FIG. 2), the scintillation crystal array may include a plurality of scintillation crystals (also referred to as "detector crystal"). The scintillation crystals may be configured to convert incident photons of radiations into scintillation lights. The first photosensor array 210 and the second photosensor array 220 may be configured to convert the scintillation lights into the electrical signals.

In some embodiments, each of the first photosensor array 210 and the second photosensor array 220 may include two or more detection units. For example, the first photosensor array 210 may at least include detection units 211 and detection units 212, the second photosensor array 220 may at least include detection units 221 and detection units 222. In some embodiments, each detection unit may correspond to one code for identifying the position of the detection unit.

In some embodiments, the corresponding relationship between the scintillation crystals and the detection units of the first photosensor array 210 and/or the second photosensor array 220 may not be limited. For example, the corresponding relationship may be any one of one-to-one, one-to-many, many-to-one, many-to-many or any combination thereof. For example, for the detection units of the first photosensor array 210 or the second photosensor array 220, one detection unit may be configured to detect scintillation lights from one scintillation crystal. Alternatively, one detection unit may be configured to detect scintillation lights from two or more scintillation crystals. Alternatively, the scintillation lights from one scintillation crystal may be detected by two or more detection units. Alternatively, one detection unit may be configured to detect the scintillation lights from two or more scintillation crystals, and the scintillation lights from one scintillation crystal may be detected by two or more detection units.

In some embodiments, the first photosensor array 210 may include a first part and a second part, and the second photosensor array 220 may include a third part and a fourth part. In some embodiments, the amount of detection units included in the first part, the second part, the third part and the fourth part may be the same. For example, the first photosensor array 210 and the second photosensor array 220 may be photosensor arrays as shown in FIG. 8. The structures and codes of the first part of the first photosensor array 210 and the third part of the second photosensor array 220 may be illustrated as 810. The structures and codes of the second part of the first photosensor array 210 and the fourth part of the second photosensor array 220 may be illustrated as 820. The amounts of the detection units included in the first part, the second part, the third part, and the fourth part may all be 7*16. In some embodiments, when the first part, the second part, the third part, and the fourth part include a same amount of the detection units, the uniformity of the readout units (e.g., the first readout unit and the second readout unit described below) for reading out the electrical signals of each part may be realized, that is, configurations of the readout units may be the same.

In some embodiments, the amounts of the detection units included in the first part, the second part, the third part and the fourth part may not be exactly the same. For example, some or all of the first part, the second part, the third part and the fourth part may include different amounts of the detection units.

In some embodiments, the amount of the detection units of the first part may be not equal to the amount of the detection units of the second part, the amount of the detection units of the third part may be not equal to the amount of the detection units of the fourth part, and the amount of detection units of the first part may be equal to the amount of detection units in the fourth part, and the amount of detection units of the second part may be equal to the amount of detection units of the third part. For example, the first photosensor array 210 and the second photosensor array 220 may be photosensor arrays as shown in FIG. 12, wherein 1210 may illustrate the first part and the fourth part, 1220 may illustrate the second part and the third part, the amount of the detection units included in the first part and the amount of the detection units included in the fourth part may be 8*15, and the amount of detection units included in the second part and the amount of the detection units included in the third part may be 8*17. In some embodiments, when the amounts of detection units included in the first part, the second part, the third part, and the fourth part are not identical, the readout units (e.g., the first readout unit and the second readout unit described below) for reading out the electrical signals of each part are not identical, that is, the configurations of the readout units may be different.

Figure 4:
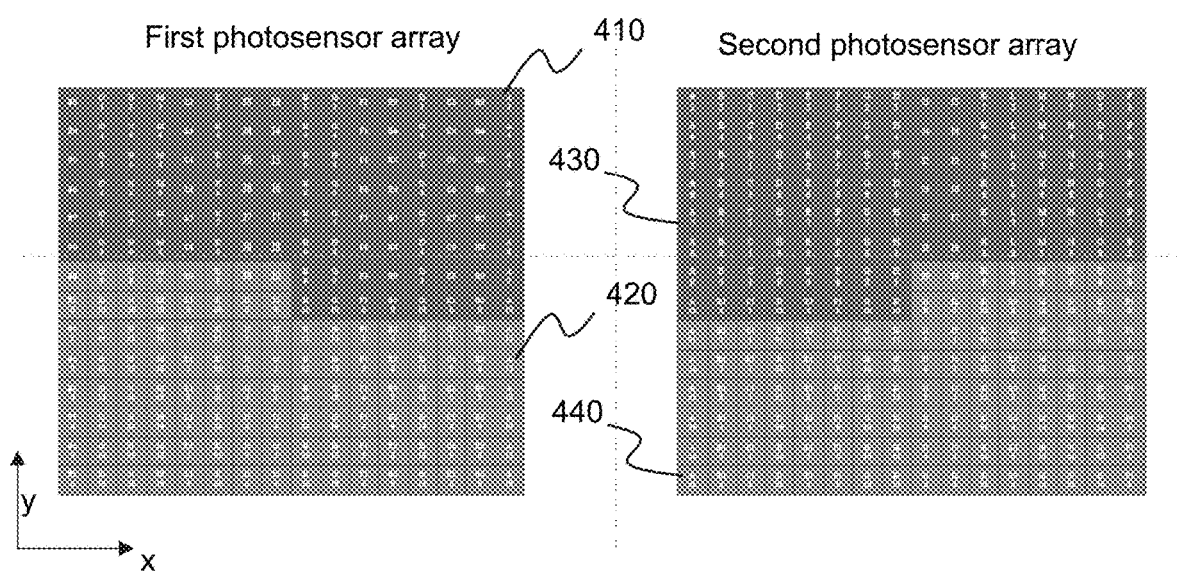
FIG. 4 is a schematic diagram illustrating a photosensor array according to some embodiments of the present disclosure.
Figure 6A:
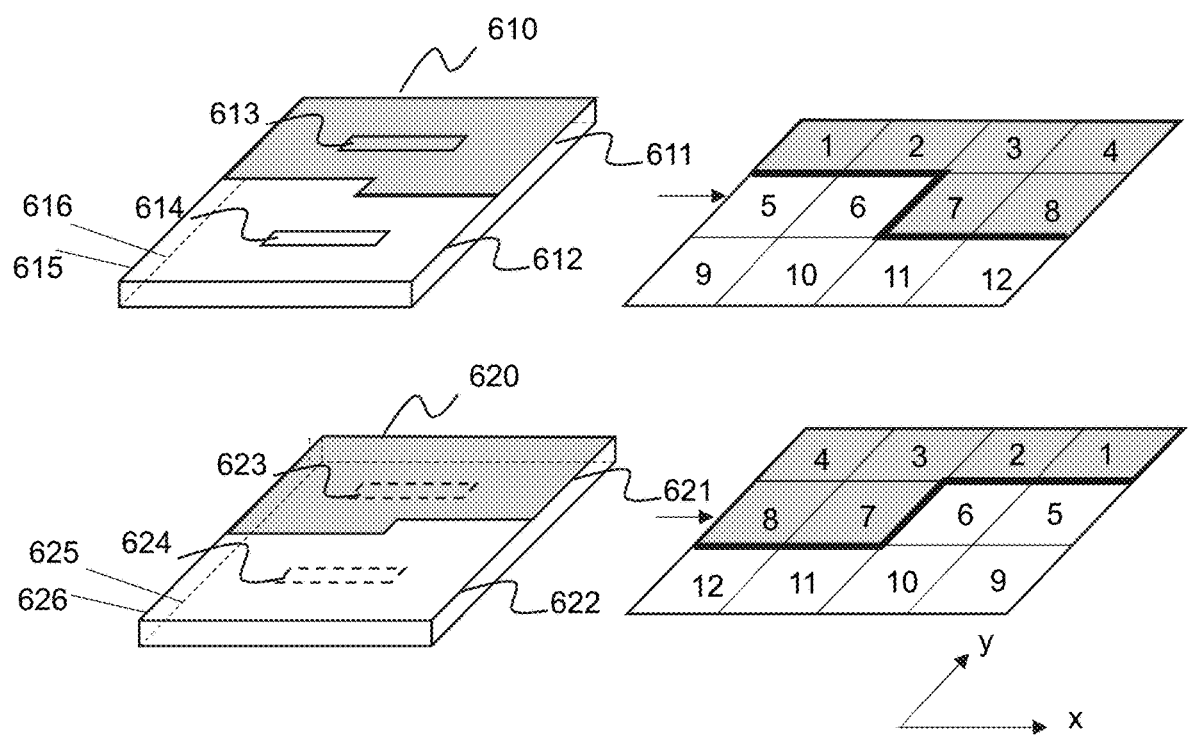
FIG. 6A and FIG. 6B are schematic diagrams illustrating the coding of photosensor arrays according to some embodiments of the present disclosure.
Figure 6B:
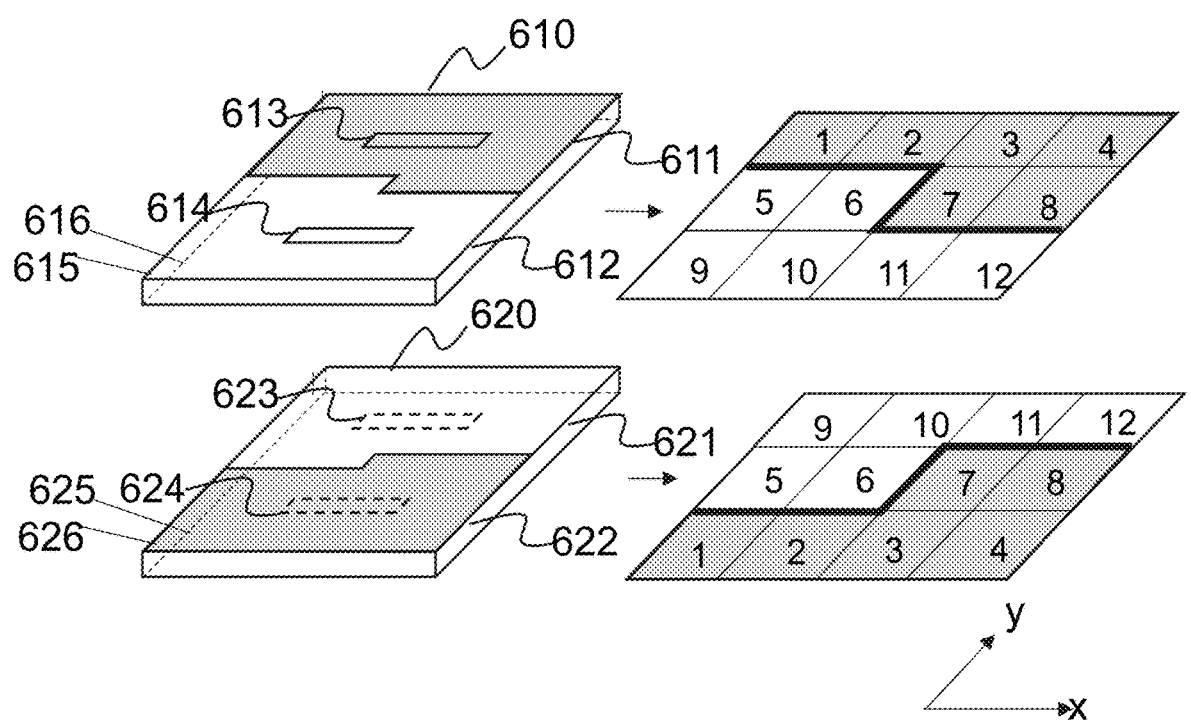

More descriptions about the first part, the second part, the third part and the fourth part, reference may be found in FIG. 4, FIG. 6A and FIG. 6B and their related descriptions.

In some embodiments, the readout module 230 may be configured to process the electrical signals output by the first photosensor array 210 and the second photosensor array 220. For example, the readout module 230 may read the electrical signals output by the detection units of the first photosensor array 210 and the second photosensor array 220, decode and output the positions of the detection units of the electrical signals based on the codes corresponding to the detection units.

In some embodiments, the readout module 230 may include a first readout unit 231 and a second readout unit 232, and configurations of the first readout unit 231 and the second readout unit 232 may be the same. The same configurations of the first readout unit 231 and the second readout unit 232 may indicate that structures of the first readout unit 231 and the second readout unit 232 and readout logics for the electrical signals are the same. For example, the positions of the signal interfaces of the first readout unit 231 and the second readout unit 232, the amount of the signal interfaces, and the amount of the detection units that can be read by each signal interface may be completely the same. For another example, when preparing the second readout unit 232, the second readout unit 232 may be obtained by duplicating the first readout unit 231, resulting in being identical to the first readout unit 231. The duplicating may mean to obtain integrated circuits or semiconductor devices with the same structures through the same design schemes. By using the same readout unit for reading electrical signals of different parts under the preset way of coding, uniformity of the readout plates may be realized, which reduces the complexity of design and maintenance of the detector system in medical imaging device (e.g., PET, SPECT, etc.), and effectively reduces costs of design and maintenance.

In some embodiments, the configurations of the first readout unit 231 and the second readout unit 232 may be different, wherein the difference may be that at least one of hardware structures and the readout logics of the electrical signals (that is, the software configuration) is different. For example, the first photosensor array 210 and the photosensor array 220 may each be a photosensor array as shown in FIG. 12. Because the first part, the second part, the third part, and the fourth part are not identical, the first readout unit 231 and the second readout unit 232 may have different hardware structures and electrical signal readout logics, or may have the same hardware structures but different electrical signal readout logics. More details regarding whether readout units are identical can be found elsewhere in connection with the description of FIG. 5.

The first readout unit 231 may be configured to process the electrical signals output by a part of the first photosensor array 210 and the electrical signals output by a part of the second photosensor array 220. The second readout unit 232 may be configured to process the electrical signals output by another part of the first photosensor array 210 and the electrical signals output by another part of the second photosensor array 220.

In some embodiments, the first readout unit 231 may process the electrical signals of the detection units of the first part of the first photosensor array 210 and the electrical signals of the detection units of the third part of the second photosensor array 220. The second readout unit 232 may process the electrical signals of the detection units of the second part of the first photosensor array 210 and the electrical signals of the detection units of the fourth part of the second photosensor array 220.

In some embodiments, the detector system 200 may include a main control module (not shown in FIG. 2), and the main control module may be connected (e.g., electrically connected) to the readout module 230.

In some embodiments, the main control module may be configured to determine radiation photon information according to the readout signals of the readout module 230, such as incident positions, energy depositions, incident times, action depth information of radiation photon in the scintillation crystals.

In some embodiments, for SPECT imaging, the main control module may send the determined radiation photon information to the processing device 120 to reconstruct the image.

In some embodiments, for PET imaging, the detector system 200 may also include coincidence boards (not shown in FIG. 2), the main control module may send the determined radiation photon information to the coincidence boards, and the coincidence boards may determine coincidence events according to the radiation photon information, and then send the coincidence events to the processing device 120 to reconstruct the image.

For PET imaging, prior to scanning, the target subject (e.g., a patient) may be injected with radioactive sources (e.g., radioactive tracer isotope). During decay, the radioactive tracer isotope may emit one or more positrons. After travelling a short distance (e.g., about 1-3 mm) inside the target object, these positrons may interact with electrons, annihilate and generate photons (for example, the annihilation of a positron may produce a pair of γ photons, each γ photon with an energy of 511 keV). The annihilation event may be referred to as a radiation event. At the same time, the γ photons of the same pair may move in opposite directions and may be received by the detector system 200. A moving path of the pair of γ photons may be called a response line, and same pairs of γ photons received or detected by two detection units located on the same response line may be called one coincidence event. After receiving the γ photons, the detection units of the detector system 200 may record time of receiving the γ photons, and convert the optical signals into electrical signals, such as timing pulses. Subsequently, the electrical signals, such as timing pulses, may be transmitted to the coincidence circuits for screening, and coincidence judgments may be made based on coincidence time windows to determine the coincidence events.

In some embodiments, the detector system 200 may include a scanning area for accommodating target objects. The scintillation crystal arrays may be arranged around an axis of the scanning area. The axis of the scanning area may correspond to a direction in which the target object is transported into or out of the scanning area.

The first photosensor array 210, the second photosensor array 220, and the scintillation crystal arrays may respectively be arranged in a ring around the axial direction of the scanning area. The first photosensor array 210 and the second photosensor array 220 may be radially located at two ends of the scintillation crystal arrays, respectively. For example, the scintillation crystal arrays may be located radially between the first photosensor array 210 and the second photosensor array 220. The first photosensor array 210 and the second photosensor arrays may be respectively located at the first end (e.g., the end away from the target object) and the second end (e.g., the end near the target object) of the scintillation crystal array, forming the double-ended readout detector.

Figure 3:
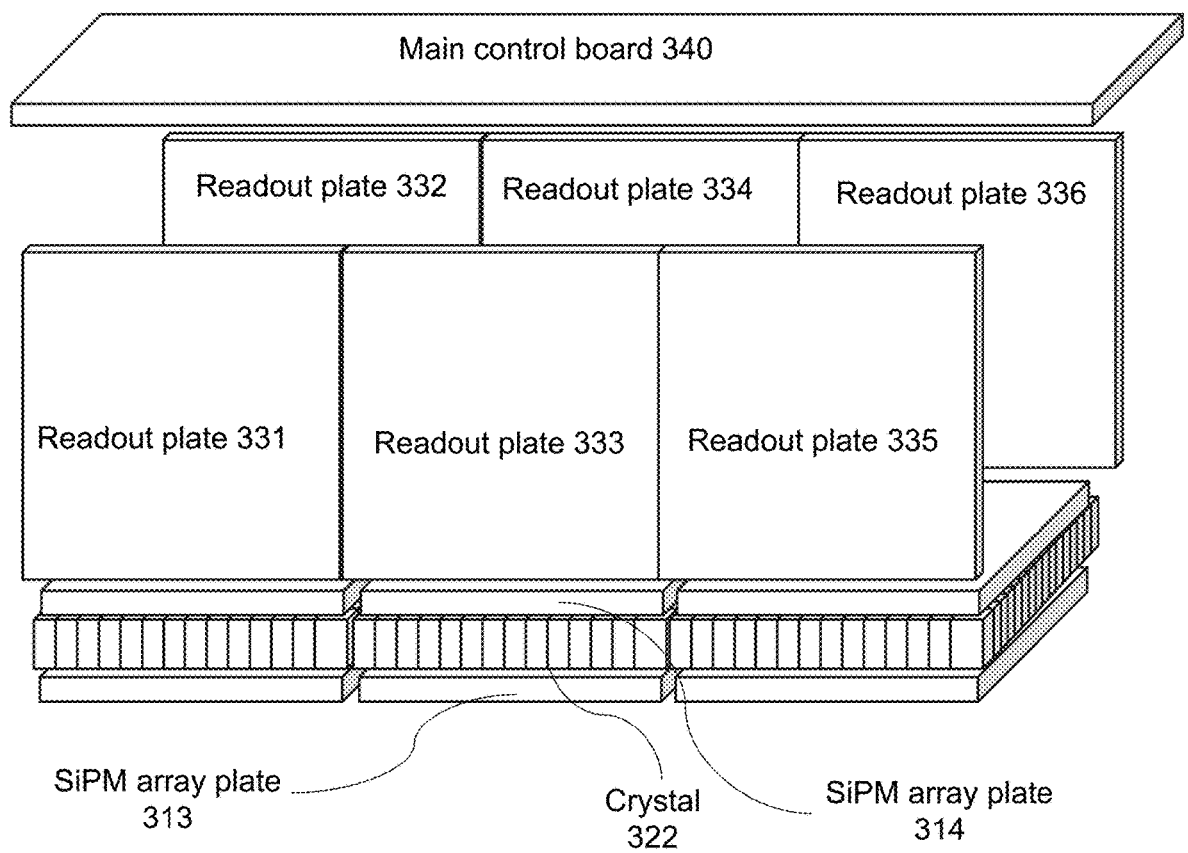
FIG. 3 is a schematic diagram illustrating a structure of a detector system according to some embodiments of the present disclosure.

FIG. 3 is a schematic diagram illustrating a structure of a detector system according to some embodiments of the present disclosure. In some embodiments, the detector system 200 may be implemented according to a detector system 300. Optionally, the detector system 200 may include a plurality of detector systems 300 arranged around an axis, and the plurality of detector systems 300 surround a substantially cylindrical scanning area.

In some embodiments, the detector system 300 may include a first photosensor array, a second photosensor array, a scintillation crystal array, a readout module, and a main control module.

The first photosensor array may include a first SiPM array plate (e.g., the SiPM array plate 313) among a plurality of SiPM array plates (also referred to as photosensor array plates), and the second photosensor array may include a second SiPM array plate (e.g., the SiPM array plate 314) among the plurality of SiPM array plates. Each SiPM array plate may include one or more detection units.

The readout module may include a first readout unit and a second readout unit. The first readout unit may include a first readout plate (e.g., the readout plate 331, the readout plate 333, the readout plate 335) among a plurality of readout plates, the second readout unit may include a second readout plate (e.g., the readout plate 332, the readout plate 334, the readout plate 336) among the plurality of readout plates, and the scintillation crystal array may include two or more scintillation crystals (e.g., the crystals 322).

In some embodiments, the first SiPM array plate and the second SiPM array plate may be respectively located at a first end (e.g., one end away from the target object) and a second end (e.g., one end near the target object) of the scintillation crystal array.

In some embodiments, the first readout plate (e.g., the readout plate 333) may be configured to process electrical signals output by a part of the first SiPM array plate (e.g., the SiPM array plate 313) and electrical signals output by a part of the second SiPM array plate (e.g., the SiPM array plate 314). The second readout plate (e.g., the readout plate 334) may be configured to process electrical signals output by another part of the first SiPM array plate (e.g., the SiPM array plate 313) and the electrical signal output by another part of the second SiPM array plate (e.g., the SiPM array plate 314). In some embodiments, the amount of the SiPM array plates and the amount of the readout plates may be the same, for example, both are integer multiple of 2.

In some embodiments, as shown in FIG. 3, the first readout plate and the second readout plate may be located on the same side of the scintillation crystals (e.g., the side away from the target object).

In some embodiments, the main control module may include one or more main control boards, which are connected (electrically connected) to all signal readout plates, and may be configured to process the readout signals output by the readout plates (e.g., the radiation photon information is determined according to the readout signals). For example, the main control boards 340 may be electrically connected to the readout plates 331-336. Optionally, an accommodation channel may be formed between the main control board 340, the readout plates 331-336, and the SiPM array plate 314, and cooling air may be input into the accommodation channel for cooling or drying the main control board 340, the readout plates 331-336, and the SiPM array plate 314.

Figure 5:
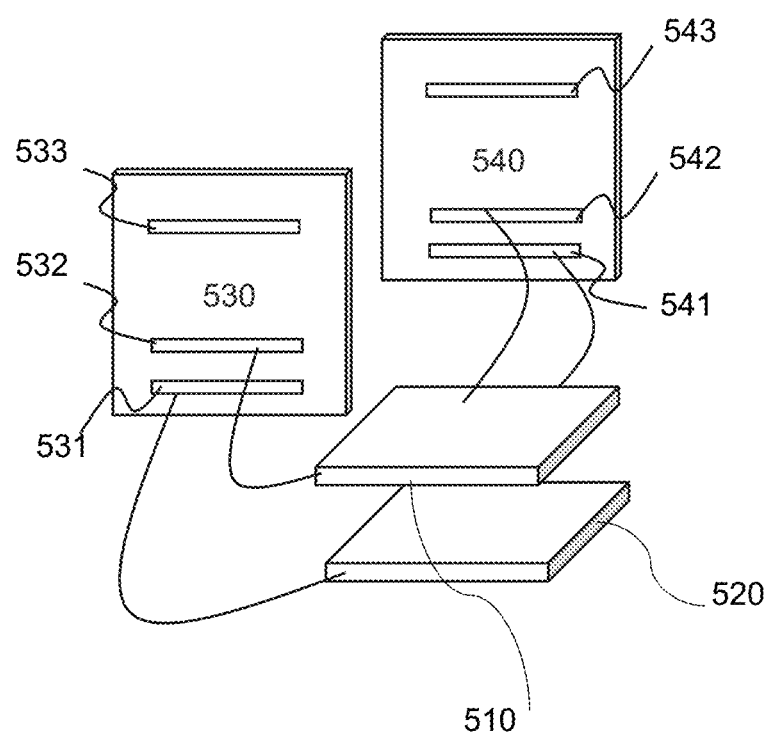
FIG. 5 is a schematic diagram illustrating connections of assemblies of a detector system according to some embodiments of the present disclosure.

Taking FIG. 5 as an example, the first readout plate 530 may be electrically connected with the first SiPM array plate 510 and the second SiPM array plate at one side, and read out the electrical signals output by a part of the detection units of the first SiPM array plate 510 and the second SiPM array plate 520. The second readout plate 540 may be electrically connected with the first SiPM array plate 510 and the second SiPM array plate 520 at another side, and read out the electrical signals output by another part of the detection units of the first SiPM array plate 510 and the second SiPM array plate 520.

FIG. 5 is a schematic diagram illustrating connections of assemblies of a detector system according to some embodiments of the present disclosure.

As shown in FIG. 5, in a detector system 500, the first readout plate 530 may include an interface 531 and an interface 532, which are respectively configured to connect a part of detection units of the first SiPM array plate 510 and the second SiPM array plate 520. The first readout plate 530 may also include an interface 533 for connecting to a main control module. The second readout plate 540 may include an interface 541 and an interface 542, which are respectively configured to connect another part of detection units of the first SiPM array plate 510 and the second SiPM array plate 520. The second readout plate 540 may also include an interface 543 for connecting to the main control module. The first readout plate 530 may be connected with the first SiPM array plate 510 and the second SiPM array plate 520 through a flexible circuit board, and the flexible circuit board are equipped with plugs, which are respectively configured to connect with the interface 531, the interface 532, the interface 541, and the interface 542. Each interface on a photosensor array plate may be used to transmit electrical signals generated by the corresponding detection units it connects to, for example, the interface of a readout plate (e.g., the first readout plate 530, the second readout plate 540) through the flexible circuit board.

It should be noted that the above descriptions are only for illustration and description, and do not limit the scope of application of the present disclosure. For those skilled in the art, various modifications and changes may be made under the guidance of the present disclosure. However, such modifications and changes are still within the scope of the present disclosure. For example, for PET imaging, the detector system 300 may also include coincidence circuits.

FIG. 4 is a schematic diagram illustrating a photosensor array according to some embodiments of the present disclosure.

As shown in FIG. 4, a photosensor array 400 may include a first photosensor array and a second photosensor array. In some embodiments, the first photosensor array may be the first photosensor array 210 and the second photosensor array may be the second photosensor array 220.

In some embodiments, the first photosensor array and the second photosensor array may each be divided into two parts. The electrical signals of the two parts of each photosensor array may be read out by two different readout plates (e.g., the first readout plate 530 and the second readout plate 540). In some embodiments, each photosensor array may be divided into two parts with equal areas along a same direction (e.g., a first direction). By doing so, it can realize the uniformity of the two different readout plates (or two different readout units) in that two corresponding interfaces of the two different readout plates, e.g., the interface 532 of the first readout plate 530 and the interface 542 of the second readout plate 540, can connect to and read out the electrical signals of the same amount of detection units. For examples, as shown in FIG. 4, the first photosensor array may be divided photosensor array into the first part 410 and the second part 420 along the first direction (i.e., the y direction). The second photosensor array may be divided photosensor array into the third part 430 and the fourth part 440 along the same first direction.

FIG. 8 is a schematic diagram illustrating a photosensor array according to some embodiments of the present disclosure.

In some embodiments, the photosensor array as shown in FIG. 8 may be an alternative example of the first photosensor array and/or the second photosensor array in FIG. 4, wherein, the first part 410 and/or the third part 430 in FIG. 4 may be replaced by a first part 810 in FIG. 8, the second part 420 and/or the fourth part 440 in FIG. 4 may be replaced by a second part 820 in FIG. 8, each cell (square grid) in FIG. 8 corresponds to a detection unit. Numbers in the cell may be codes of the detection units, and every 2*2 detection units may form a detector unit such as $$\begin{bmatrix} P3 & O3 \\ P4 & O4 \end{bmatrix}, \begin{bmatrix} D9 & C9 \\ D10 & C10 \end{bmatrix}.$$

In some embodiments, a main control module may read signals of the detector units in the first photosensor array and the second photosensor array that are disposed opposite to each other, use a difference between the readout signals at both ends (i.e., the opposite detector units) to calculate an action depth information of the γ photon in a crystal, so as to realize the acquisition of the three-dimensional action position information of the γ photon. For example, as shown in FIG. 8, the position of the detector unit $$\begin{bmatrix} P3 & O3 \\ P4 & O4 \end{bmatrix}$$

in the first photosensor array may be opposite to the position of the detector unit $$\begin{bmatrix} B3 & A3 \\ B4 & A4 \end{bmatrix}$$

in the second photosensor array, the main control module may obtain the signal difference of the two detector units, use the difference to calculate the action depth information of γ photons in the crystal between the two detector units.

In some embodiments, the first photosensor array and the second photosensor array may each be divided into two parts with unequal areas along a same direction. For example, the first photosensor array and the second photosensor array may be photosensor arrays as shown in FIG. 12, and the areas of the two parts 1210 and 1220 may be not equal. 1210 may be the first part and the fourth part, 1220 may be the second part and the third part. The first readout unit 231 may process the electrical signals of the detection units of the first part and the third part, and the second readout unit 232 may process the electrical signals of the detection units of the second part and the fourth part. In some embodiments, when the first photosensor array and the second photosensor array are divided into two parts with unequal areas, the first readout unit and the second readout unit may not be identical, that is, the configurations of the first readout unit and the second readout unit may be different. In such cases, all the photosensor array plates can be uniformly designed and prepared, and different readout units may be designed and prepared differently. In some embodiments, even if the first photosensor array and the second photosensor array are divided into two parts with unequal areas, the first readout unit and the second readout unit may still be identical, provided that each interface (e.g., each of the interfaces 531, 532, 541, 542) on the first readout unit and the second readout unit are capable of reading out the signals of all detection units in the part with the larger area. In such cases, the configurations of the first readout unit and the second readout unit may still be same, and each of the first readout unit and the second readout unit can meet the reading requirements for the first photosensor array and the second photosensor array.

In some embodiments, the detection units of each of the first part, the second part, the third part and the fourth part may include at least two blocks of detection units that are distributed discontinuously. For example, the first photosensor array (or the second photosensor array) may be the photosensor array shown in FIG. 10, wherein, 1010-1 (the upper left area delimited by two bold solid lines except the area 1020-3), 1010-2 (the bottom right area delimited by two bold solid lines), 1010-3 (the area delimited by dotted lines) and 1010-4 (the area delimited by dotted lines) together form the first part (or the third part), 1020-1 (the upper right area delimited by two bold solid lines except the area 1010-3), 1020-2 (the bottom left area delimited by two bold solid lines except the area 1010-4) and 1020-3 (the area delimited by dotted lines) together form the second part (or the fourth part). It may be seen that the first part (or the third part) includes four discontinuous blocks of detection units, and the second part (or the fourth part) includes three discontinuous blocks of detection units. For another example, the first photosensor array (or the second photosensor array) may be the photosensor array shown in FIG. 11, wherein, 1110-1 (the upper left area delimited by two bold solid lines except the area 1120-3), 1110-2 (the bottom right area delimited by two bold solid lines) and 1110-3 (the area delimited by dotted lines) together form the first part (or the third part), 1120-1 (the upper right area delimited by two bold solid lines), 1120-2 (the bottom left area delimited by two bold solid lines except the area 1110-3) and 1120-3 (the area delimited by dotted lines) together form the second part (or the fourth part), it may be seen that the first part (or the third part) includes three discontinuous detection units, and the second part (or the fourth part) includes three discontinuous detection units.

In some embodiments, when the first part, the second part, the third part and the fourth part include discontinuously distributed detection units, if the first photosensor array and the second photosensor array are divided into two parts with equal areas (that is, the areas of the first part and the second part are equal, the areas of the third part and the fourth part are equal), the readout units may still be uniformly designed and prepared. If the first photosensor array and the second photosensor array are divided into two parts with unequal areas, the readout units may not be uniformly designed and prepared. Regardless of whether the readout units are uniform or not, the main control module may read the signals of the detector units at opposite ends of each photosensor array, use the difference in the magnitude of the readout signals at both ends to perform calculations to obtain depth information about action of γ photons in the crystal.

In some embodiments, shapes of the first part and the second part may be asymmetric, and shapes of the third part and the fourth part may be asymmetric. For example, in the case where the first part, the second part, the third part and the fourth part as shown in FIG. 10 and FIG. 11 include discontinuous detection units, shapes of two parts from a same photosensor array are asymmetric. For another example, as shown in FIG. 12, the first part and the third part may be 1210, the second part and the fourth part may be 1220. Since the amounts of detection units of two parts from a same photosensor array are not equal, the corresponding shapes are asymmetric.

In some embodiments, the division of the first part and the second part, which is same as the division of the third part and the fourth part, may be carried out by preset rules. In some embodiments, a boundary between the first part and the second part, a boundary between the third part and the fourth part may be discontinuous, and the discontinuous boundary may make each of the detection units of the first part, the second part, the third part and the fourth part include at least two detection units distributed discontinuously.

In some embodiments, the first photosensor array (or the second photosensor array) may be divided into two parts according to a first preset rule, wherein the first preset rule may include a discontinuous boundary. For example, first photosensor array (or the second photosensor array) may be the photosensor array as shown in FIG. 10, and the first preset rule may be the discontinuous boundary, which divides the first photosensor array (or the second photosensor array) into the first part including 1010-1, 1010-2, 1010-3 and 1010-4, and the second part including 1020-1, 1020-2 and 1020-3. In some embodiments, the first photosensor array (or the second photosensor array) photosensor array may be divided into two parts according to a second preset rule, wherein the second preset rule may include a continuous boundary. For example, the first photosensor array (or the second photosensor array) may be the photosensor array as shown in FIG. 12, and the second preset rule may be the continuous boundary, which divides the first photosensor array (or the second photosensor array) into the first part including 1210, and the second part including 1220.

In some embodiments, the detection units of the first part 410 of the first photosensor array and the detection units of the third part 430 of the second photosensor array may be encoded in a same way, the detection units of the second part 420 of the first photosensor array and the detection units of the fourth part 440 of the second photosensor array may be encoded in a same way. In some embodiments, that the detection units are encoded in a same way may refer to the same coding sequence. For example, the first part 410 of the first photosensor array and the third part 430 of the second photosensor array may include detection units with a size of 7*16 which are encoded according to the manner in the first part 810 in FIG. 8. The second part 420 of the first photosensor array and the fourth part 440 of the second photosensor array may include detection units with a size of 7*16 which are encoded according to the manner in the second part 820 in FIG. 8.

In some embodiments, the detection units of the first part 410 of the first photosensor array and the detection units of the fourth part 440 of the second photosensor array may be encoded in a same way, the detection units of the second part 420 of the first photosensor array and the detection units of the third part 430 of the second photosensor array may be encoded in a same way. For example, the first part 410 of the first photosensor array and the fourth part 440 of the second photosensor array may include detection units with a size of 7*16 which are encoded according to the manner in the first part 810 in FIG. 8. The second part 420 of the first photosensor array and the third part 440 of the second photosensor array may include detection units with a size of 7*16 which are encoded according to the manner in the second part 820 in FIG. 8.

In some embodiments, the division of the first photosensor array and the second photosensor array may make the detection units photosensor array are not separated into different parts. For example, as shown in FIG. 8, a photosensor array with a size of 14*16 may be divided into a first part 810 and a second part 820 along a broken solid line, instead of being divided along a straight line traversing the center of the photosensor array. In this way, one detector unit (e.g., $$\begin{bmatrix} D9 & C9 \\ D10 & C10 \end{bmatrix})$$

are not separated into the first part 810 and the second part 820 respectively, but being grouped into the first part 810 as a whole. The above-mentioned broken solid line first extends along the x direction, then extends along the y direction, and then extends along the x direction again. The broken solid line may divide the photosensor array into the first part and the second part, or the third part and the fourth part.

In some embodiments of the present disclosure, using the photosensor array plates with an identical structure at both ends of the crystal may realize the double-ended readout, and the uniformity of the double-ended photosensor array plates of the detector system in the medical imaging device (e.g., PET, SPECT) can be successfully realized and the costs of design and maintenance may be reduced.

In some embodiments, shapes of the first part 410 and the second part 420 may be symmetrical about the center of the first photosensor array, and shapes of the third part 430 and the fourth part 440 may be symmetrical about the center of the second photosensor array. In such cases, the amounts of detection units included in the first part, the second part, the third part, and the fourth part may be the same.

FIG. 6A and FIG. 6B are schematic diagrams illustrating codes of photophotosensor arrays according to some embodiments of the present disclosure. The x-direction and y-direction in FIG. 6A and FIG. 6B correspond to the x-direction and y-direction in FIG. 4.

In some embodiments, the first part of the first photosensor array may include a first interface, the second part of the first photosensor array may include a second interface, the third part of the second photosensor array may include a third interface, and the fourth part of the second photosensor array may include a fourth interface. A readout module may be connected to the first photosensor array and the second photosensor array through the first interface, the second interface, the third interface and the fourth interface to read the electrical signals of corresponding parts.

As shown in FIG. 6A and FIG. 6B, photosensor array the first photosensor array 610 may be divided into a first part 611 and a second part 612 along a first direction (e.g., the y-direction), photosensor array the second photosensor array 620 may be divided into a third part 621 and a fourth part 622 along the first direction (e.g., the y-direction).

The first part 611 of the first photosensor array 610 may include an interface 613, the second part 612 of the first photosensor array 610 may include an interface 614, the third part 621 of the second photosensor array 620 may include an interface 623, the fourth part 622 of the second photosensor array 620 may include an interface 624. Each interface on a photosensor array (e.g., the first photosensor array 610, the second photosensor array 620) may be used to transmit electrical signals generated by the corresponding detection units it connects to the interface of a readout plate (e.g., the first readout plate 530, the second readout plate 540) through, for example, a flexible circuit board.

The first photosensor array 610 may include a first surface 615 and a second surface 616, and the position of the first surfaces 615 is opposite to the position of the second surface 616. The second photosensor array 620 may include a third surface 625 and a fourth surface 626, and the position of the third surfaces 625 is opposite to the position of the fourth surface 626.

In some embodiments, the first interface 613 and the second interface 614 of the first photosensor array 610 may be arranged on the first surface 615 of the first photosensor array 610, and the third interface 623 and the fourth interface 624 of the second photosensor array 620 may be arranged on the third surface 625 of the second photosensor array 620. In some embodiments, for the first surface 615 and the second surface 616 of the first photosensor array 610, and the third surface 625 and the fourth surface 626 of the second photosensor array 620, the surfaces without the interfaces may be oppositely arranged. For example, the second surface 616 of the first photosensor array 610 and the fourth surface 626 of the second photosensor array 620 may be disposed opposite to each other.

As shown in FIG. 6A and FIG. 6B, the first readout unit may be connected with the first part 611 of the first photosensor array 610 and the third part 621 of the second photosensor array 620. The second readout unit may be connected to the second part 612 of the first photosensor array 610 and the fourth part 622 of the second photosensor array 620.

As shown in FIG. 6A and FIG. 6B, when the first photosensor array 610 and the second photosensor array 620 are installed in the detector system, the position of the first part 611 of the first photosensor array 610 is disposed opposite to the position of the third part 621 of the second photosensor array 620, and the position of the second part 612 of the first photosensor array 610 may correspond to the position of the fourth part 622 of the second photosensor array 620. For example, the first part 611 of the first photosensor array 610 and the third part 621 of the second photosensor array 620 are located at the same side of the first photosensor array 610 and the second photosensor array 620, respectively, along the y-direction.

As shown in FIG. 6A, the first photosensor array 610 and the second photosensor array 620 may respectively include detector units with a size of 3*4. The first part 611 may include detector units coded as (1, 2, 3, 4, 7, 8), the second part 612 may include detector units coded as (5, 6, 9, 10, 11, 12). The third part 621 may include detector units coded as (1, 2, 3, 4, 7, 8), the fourth part 622 may include detector units coded as (5, 6, 9, 10, 11, 12). Clearly, the coding sequence of the detecting units photosensor array included in the first part 611 may be symmetrical to the coding sequence of the detecting units photosensor array included in the third part 621 with respect to the first direction (e.g., the y-direction). As shown in FIG. 6A, the coding sequence of the detector units (1, 2, 3, 4, 7, 8) included in the first part 611 in the x-direction and y-direction may be symmetrical to the coding sequence of the detector units (1, 2, 3, 4, 7, 8) included in the third part 621 in the x-direction and y-direction with respect to the first direction (e.g., the y-direction). That is, after the first part 611 is flipped by 180 degrees around the axis in the first direction (e.g., the y-direction), it may coincide with the third part 621. Similarly, the coding sequence of the detection units photosensor array included in the second part 612 may be symmetrical to the coding sequence of the detection units photosensor array included in the fourth part 622 with respect to the first direction. As shown in FIG. 6A, the coding sequence of the detector units (5, 6, 9, 10, 11, 12) included in the second part 612 in the x-direction and y-direction may be symmetrical to the coding sequence of the detector units (5, 6, 9, 10, 11, 12) included in the fourth part 622 in the x-direction and y-direction with respect to the first direction (e.g., the y-direction). That is, after the second part 612 is flipped by 180 degrees around the axis in the first direction (e.g., the y-direction), it may coincide with the fourth part 622. Accordingly, by flipping the first photosensor array 610 by 180 degrees around the axis in the y-direction, the first photosensor array 610 may completely overlap with the second photosensor array 620.

In order to realize the practicability on the hardware, the interfaces on the first photosensor array 610 and the second photosensor array 620 need to face to the side away from the scintillation crystal array respectively. Since the configurations of the first photosensor array 610 and the second photosensor array 620 are the same, when the position of the first photosensor array 610 is opposite to the position of the second photosensor array 620, the position of the first part 611 of the first photosensor array 610 may correspond to the position of the third part 621 of the second photosensor array 620, the position of the second part 612 of the first photosensor array 610 may correspond to the position of the fourth part 622 of the second photosensor array 620, and the interfaces on the first photosensor array 610 and the second photosensor array 620 respectively face the side away from the scintillation crystal array. In the assembly shown in FIG. 6A, the second photosensor array 620 in the detector system may be understood as flipping the first photosensor array 610 around the axis in the y-direction by 180 degrees. Therefore, in the above assembly, the coding sequence of the detection units (1, 2, 3, 4, 7, 8) included in the first part 611 in the x-direction and y-direction may be symmetrical to the coding sequence of the detection units (1, 2, 3, 4, 7, 8) included in the third part 621 in the x-direction and y-direction with respect to the first direction (e.g., the y-direction). The coding sequence of the detection units (5, 6, 9, 10, 11, 12) included in the second part 612 in the x-direction and y-direction may be symmetrical to the coding sequence of the detection units (5, 6, 9, 10, 11, 12) included in the fourth part 622 in the x-direction and y-direction with respect to the first direction (e.g., the y-direction).

As shown in FIG. 6B, the first photosensor array 610 and the second photosensor array 620 may respectively include detector units with a size of 3*4. The first part 611 may include detector units coded as (1, 2, 3, 4, 7, 8), the second part 612 may include detector units coded as (5, 6, 9, 10, 11, 12). The third part 621 may include detector units coded as (5, 6, 9, 10, 11, 12), the fourth part 622 may include detector units coded as (1, 2, 3, 4, 7, 8). Clearly, the coding sequence of the detection units included in the first part 611 may be symmetrical to the coding sequence of the detection units included in the fourth part 622 with respect to the second direction (e.g., the x-direction), wherein the second direction may be perpendicular to the first direction. As shown in FIG. 6B, the coding sequence of the detection units (1, 2, 3, 4, 7, 8) included in the first part 611 in the x-direction and y-direction may be symmetrical to the coding sequence of the detection units (1, 2, 3, 4, 7, 8) included in the fourth part 622 in the x-direction and y-direction with respect to the second direction (e.g., the x-direction). That is, after the first part 611 is flipped by 180 degrees around the axis in the second direction (e.g., the x-direction), it may coincide with the fourth part 622.

Similarly, the coding sequence of the detection units photosensor array included in the second part 612 may be symmetrical to the coding sequence of the detection units photosensor array included in the third part 621 with respect to the second direction, wherein the second direction may be perpendicular to the first direction. As shown in FIG. 6B, the coding sequence of the detector units (5, 6, 9, 10, 11, 12) included in the second part 612 in the x-direction and y-direction may be symmetrical to the coding sequence of the detector units (5, 6, 9, 10, 11, 12) included in the third part 621 in the x-direction and y-direction with respect to the second direction (e.g., the x-direction). That is, after the second part 612 is flipped by 180 degrees around the axis in the second direction (e.g., the x-direction), it may coincide with the third part 621. Accordingly, by flipping the first photosensor array 610 by 180 degrees around the axis in the x-direction, the first photosensor array 610 may completely overlap with the second photosensor array 620.

As shown in FIG. 6B, in order to realize the practicability on the hardware, the interfaces on the first photosensor array 610 and the second photosensor array 620 need to face to the side away from the scintillation crystal array respectively. Since the configurations of the first photosensor array 610 and the second photosensor array 620 are the same, when the position of the first photosensor array 610 is opposite to the position of the second photosensor array 620, the position of the first part 611 of the first photosensor array 610 may correspond to the position of the third part 621 of the second photosensor array 620, the position of the second part 612 of the first photosensor array 610 may correspond to the position of the fourth part 622 of the second photosensor array 620, and the interfaces on the first photosensor array 610 and the second photosensor array 620 respectively face the side away from the scintillation crystal array. In the assembly shown in FIG. 6B, the second photosensor array 620 in the detector system may be understood as flipping the first photoelectric photosensor array 610 by 180 degrees around the axis in the x-direction. Therefore, in the above assembly, the coding sequence of the detection units (1, 2, 3, 4, 7, 8) included in the fourth part 622 in the x-direction and y-direction may be symmetrical to the coding sequence of the detection units (1, 2, 3, 4, 7, 8) included in the first part 611 in the x-direction and y-direction with respect to the second direction (e.g., the x-direction). The coding sequence of the detection units (5, 6, 9, 10, 11, 12) included in the second part 612 in the x-direction and y-direction may be symmetrical to the coding sequence of the detection units (5, 6, 9, 10, 11, 12) included in the third part 621 in the x-direction and y-direction with respect to the second direction (e.g., the x-direction).

Figure 7:
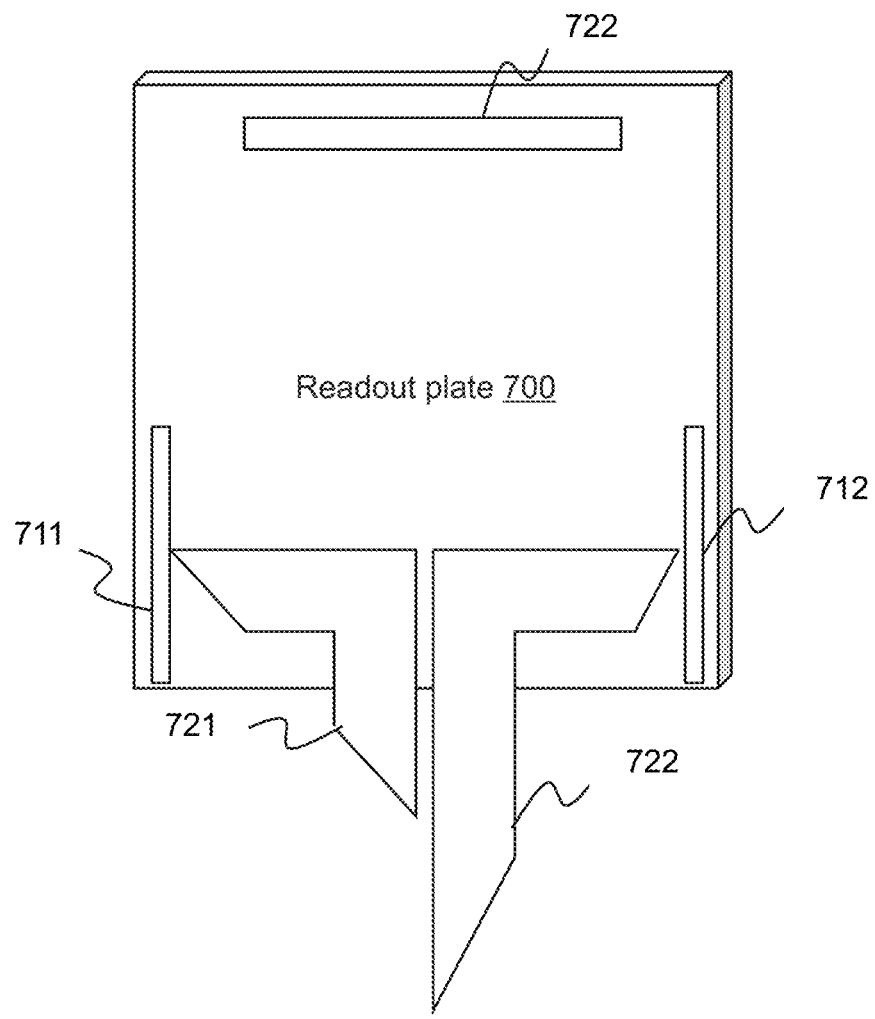
FIG. 7 is a schematic diagram illustrating connections of assemblies of a detector system according to some embodiments of the present disclosure.

FIG. 7 is a schematic diagram illustrating connections of assemblies of a detector system according to some embodiments of the present disclosure.

As shown in FIG. 7, a readout plate 700 may include an interface 711, an interface 712, and an interface 722, a connector 721 and a connector 722. The interface 711 may be connected to one of a first photosensor array and a second photosensor array through the connector 721. The interface 712 may be connected to the other of the first photosensor array and the second photosensor array through the connector 722. The interface 722 may be configured to connect a main control module.

The first photosensor array and the second photosensor array may be oppositely arranged at a first end and a second end of a scintillation crystal array, respectively. The readout plate 700 may be arranged on the first end of the scintillation crystal array. The connector 721 may be a short connector, which may be configured to connect the interface 711 and the interface of the first photosensor array located at the first end of the scintillation crystal array. As shown in FIG. 6A and FIG. 6B, the connector 721 may be inserted into an interface 613 of the first photosensor array 610, and the connector 722 may be inserted into an interface 623 of the second photosensor array 620 through the interface 613.

Having thus described the basic concepts, it may be rather apparent to those skilled in the art after reading this detailed disclosure that the foregoing detailed disclosure is intended to be presented by way of example only and isn't limiting. Various alterations, improvements, and modifications may occur and are intended for those skilled in the art, though not expressly stated herein. These alterations, improvements, and modifications are intended to be suggested by this disclosure and are within the spirit and scope of the exemplary embodiments of this disclosure.

Moreover, certain terminology has been configured to describe embodiments of the present disclosure. For example, the terms "one embodiment," "an embodiment," and/or "some embodiments" mean that a particular feature, structure, or feature described in connection with the embodiment is included in at least one embodiment of the present disclosure. Therefore, it is emphasized and should be appreciated that two or more references to "an embodiment," "one embodiment," or "an alternative embodiment" in various portions of the present disclosure are not necessarily all referring to the same embodiment. Furthermore, the particular features, structures, or features may be combined as suitable in one or more embodiments of the present disclosure.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various embodiments. This method of disclosure, however, isn't to be interpreted as reflecting an intention that the claimed subject matter requires more features than are expressly recited in each claim. Rather, claimed subject matter may lie in less than all features of a single foregoing disclosed embodiment.

In some embodiments, the numbers expressing quantities or properties configured to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the count of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present disclosure, the description, definition, and/or the use of the term in the present disclosure shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A detector system, comprising:
   a first photosensor array and a second photosensor array, wherein a position of the first photosensor array is opposite to a position of the second photosensor array, and configurations of the first photosensor array and the second photosensor array are the same, the first photosensor array and the second photosensor array are configured to output electrical signals related to radiated photons, respectively; and
   a readout module, including a first readout unit and a second readout unit, wherein the first readout unit is configured to read out signals of detection units of a first part in the first photosensor array and signals of detection units of a third part in the second photosensor array, the second readout unit is configured to read out signals of detection units of a second part in the first photosensor array and signals of detection units of a fourth part in the second photosensor array.

2. The system of claim 1, wherein an amount of the detection units of the first part, an amount of the detection units of the second part, an amount of the detection units of the third part, an amount of the detection units of the fourth part are equal.

3. The system of claim 2, wherein configurations of the first readout unit and the second readout unit are the same.

4. The system of claim 2, wherein shapes of the first part and the second part are symmetrical about a center, and shapes of the third part and the fourth part are symmetrical about the center.

5. The system of claim 2, wherein the first photosensor array is divided into the first part and the second part along a first direction.

6. The system of claim 5, wherein the second photosensor array is divided into the third part and the fourth part along the first direction.

7. The system of claim 6, wherein the detection units of the first part are encoded in a same way as the detection units of the third part, and the detection units of the second part are encoded in a same way as the detection units of the fourth part.

8. The system of claim 7, wherein a coding sequence of the detection units of the first part is symmetrical to a coding sequence of the detection units of the third part with respect to the first direction, a coding sequence of the detection units of the second part is symmetrical to a coding sequence of the detection units of the fourth part with respect to the first direction.

9. The system of claim 6, wherein the detection units of the first part are encoded in a same way as the detection units of the fourth part, and the detection units of the second part are encoded in a same way as the detection units of the third part.

10. The system of claim 9, wherein a coding sequence of the detection units of the first part is symmetrical to a coding sequence of the detection units of the fourth part with respect to a second direction, a coding sequence of the detection units of the second part is symmetrical to a coding sequence of the detection units of the third part with respect to the second direction.

11. The system of claim 2, wherein each of the detection units of the first part, the second part, the third part and the fourth part includes at least two discontinuously distributed detection units.

12. The system of claim 11, wherein shapes of the first part and the second part are asymmetric, and shapes of the third part and the fourth part are asymmetric.

13. The system of claim 11, wherein the first photosensor array is divided into the first part and the second part according to a first preset rule, and the first preset rule includes that a boundary between the first part and the second part is discontinuous.

14. The system of claim 11, wherein the second photosensor array is divided into the third part and the fourth part according to a second preset rule, and the second preset rule includes that a boundary between the third part and the fourth part is discontinuous.

15. The system of claim 1, wherein an amount of the detection units of the first part is not equal to an amount of the detection units of the second part, an amount of the detection units of the third part is not equal to an amount of the detection units of the fourth part, the amount of the detection units of the first part is equal to the amount of the detection units of the fourth part, and the amount of the detection units of the second part is equal to the amount of the detection units of the third part.

16. The system of claim 15, wherein configurations of the first readout unit and the second readout unit are different.

17. The system of claim 2, wherein the first part includes a first interface, the second part includes a second interface, the third part includes a third interface, the fourth part includes a fourth interface, and the readout module is connected to the first photosensor array and the second photosensor array through the first interface, the second interface, the third interface and the fourth interface.

18. The system of claim 17, wherein,
the first photosensor array includes a first surface and a second surface, a position of the first surface is opposite to a position of the second surface, and the second photosensor array includes a third surface and a fourth surface, a position of the third surface is opposite to a position of the fourth surface;
the first interface and the second interface are arranged on the first surface of the first photosensor array, and the third interface and the fourth interface are arranged on the third surface of the second photosensor array; and
the position of the second surface of the first photosensor array is opposite to the position of the fourth surface of the second photosensor array.

19. An imaging device, comprising a plurality of detector systems arranged around an axis and surrounding a cylindrical scanning area, wherein each detector system comprises:
a first photosensor array and a second photosensor array, wherein a position of the first photosensor array is opposite to a position of the second photosensor array, and configurations of the first photosensor array and the second photosensor array are the same, the first photosensor array and the second photosensor array are configured to output electrical signals related to radiated photons, respectively; and
a readout module, including a first readout unit and a second readout unit, wherein the first readout unit is configured to read out signals of detection units of a first part in the first photosensor array and signals of detection units of a third part in the second photosensor array, the second readout unit is configured to read out signals of detection units of a second part in the first photosensor array and signals of detection units of a fourth part in the second photosensor array.

20. The imaging device of claim 19, wherein an amount of the detection units of the first part, an amount of the detection units of the second part, an amount of the detection units of the third part, an amount of the detection units of the fourth part are equal.

* * * * *